US012636475B2

(12) United States Patent  (10) Patent No.:  US 12,636,475 B2
Karimi  (45) Date of Patent:  May 26, 2026

(54) METHOD FOR TREATING ACNE AND OTHER INFLAMMATORY SKIN CONDITIONS

(71) Applicant: HEALMD, LLC, Montgomery, TX (US)

(72) Inventor: Kian Karimi, Pacific Palisades, CA (US)

(73) Assignee: HealMD, LLC, Gardena, CA (US)

( * ) Notice: Subject to any disclaimer, the term of this patent is extended or adjusted under 35 U.S.C. 154(b) by 536 days.

(21) Appl. No.: 18/134,967

(22) Filed: Apr. 14, 2023

(65) Prior Publication Data

US 2024/0342451 A1  Oct. 17, 2024

(51) Int. Cl.
  *A61M 37/00*  (2006.01)
  *A61K 31/00*  (2006.01)

(52) U.S. Cl.
  CPC ....... *A61M 37/0015* (2013.01); *A61K 31/658* (2023.05); *A61M 2037/0023* (2013.01); *A61M 2037/0061* (2013.01)

(58) Field of Classification Search
  CPC ...... A61M 37/0015; A61M 2037/0023; A61M 2037/0061
  See application file for complete search history.

*Primary Examiner* — Bradley J Osinski
(74) *Attorney, Agent, or Firm* — Aura IP Law, PC

(57) ABSTRACT

A method for treating active acne or any other inflammatory skin condition, such as, but not limited to, rosacea, psoriasis, and the like is disclosed comprising using a microneedling device capable of achieving certain specific depths which are controllable by the user and a medical grade anti-inflammatory antibacterial antioxidant oil which is applied to the treatment area both before and after the microneedling. In a preferred embodiment, the oil is a medical grade CBD tincture with organic hempseed oil. The treatment is repeated until satisfactory resolution of the acne or any other inflammatory skin condition that is being treated has been achieved.

20 Claims, 1 Drawing Sheet

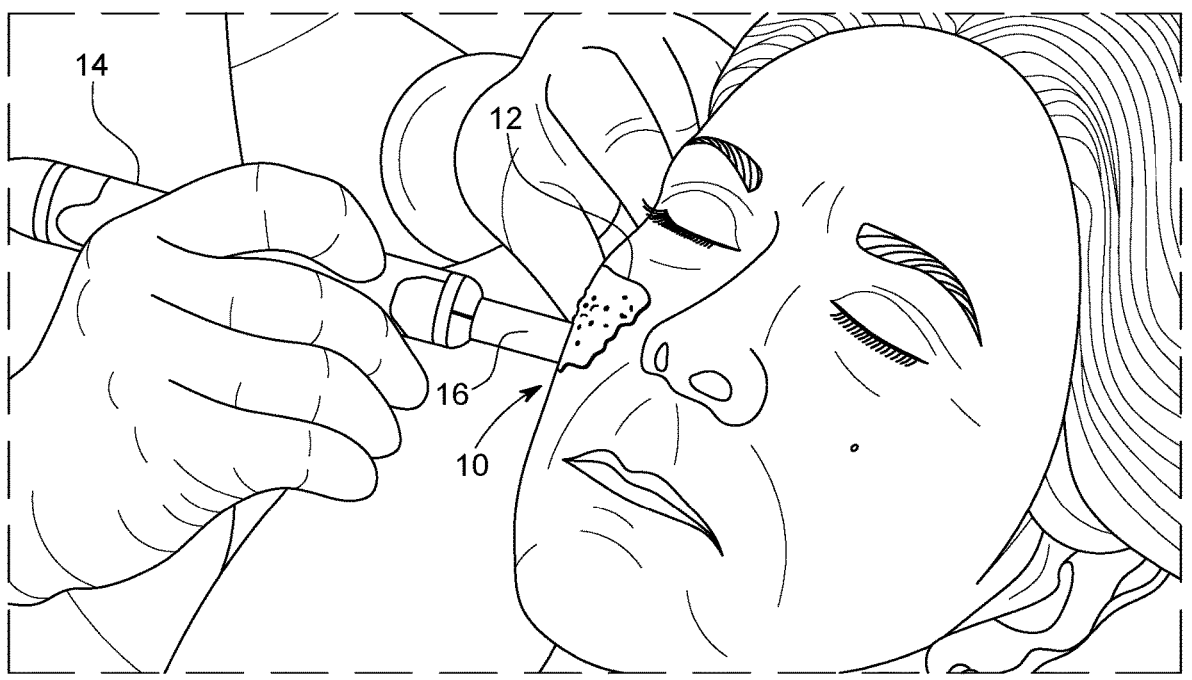

METHOD FOR TREATING ACNE AND OTHER INFLAMMATORY SKIN CONDITIONS

FIELD OF THE INVENTION

The invention relates to a method of treating inflammatory skin conditions, such as, but not limited to, acne, using a device comprising microneedle arrays or a plurality of fine needles combined with a medical grade anti-inflammatory, antibacterial, antioxidant pure oil, such as, but not limited to, medical grade pure CBD (cannabidiol) oil.

BACKGROUND OF THE INVENTION

Microneedling is a popular cosmetic procedure that involves the use of a device with one or more fine needles or microneedle arrays which are used to puncture the skin and stimulate collagen production in the surrounding tissue. There are numerous microneedling devices that use a plurality of fine needles and/or microneedle arrays combined with a specific drug formulation which is delivered to a patient transdermally for treatment. By way of example and not limitation, such a microneedling device and method is described and claimed in U.S. Pat. No. 7,658,728 (Yuzhakov, 2010), which patent discloses a microneedle array and drug delivery device for transdermal delivery of a drug formulation to a patient.

While microneedling has been used to treat a variety of skin conditions, including acne scars, wrinkles, and hyperpigmentation, none of the prior art devices or methods discuss using microneedling when active acne is present or using oils as the transdermal formulation to treat acne, as it is contraindicated in the literature and in the dermatological field in general. Specifically, in the prior art, many doctors, med spas, and other dermatology experts expressly state that microneedling should not be done when active acne is present as, by way of example and not limitation, it will open active acne sores and spread the bacteria contained within such sores to other locations causing more breakouts and potentially lead to infection.

By way of example and not limitation, on the American Academy of Dermatology Association (AADA) website located at https://www.aad.org/public/diseases/acne/derm-treat/treat, the AADA gives its treatment recommendations for acne and expressly excludes using any oil products in the presence of active acne. A review of the website at the time of writing reflects that the AADA does not mention microneedling, CBD, or the use of any oils in its recommended treatment plans for acne. In an article entitled "Acne Overview" on the AADA website at https://www.aad.org/public/diseases/acne/really-acne/overview, the AADA provides an overview of acne and states, "Use only oil-free skin care products, sunscreen, and makeup. When you have acne, you have clogged pores. If you apply anything that contains oil, you'll likely clog your pores again. Clogged pores can lead to more breakouts."

Further examples of physicians' opinions that using microneedling over acne is contraindicated in the art are located on the website www.RealSelf.com. On that site, many physicians respond to potential and current patients' questions regarding microneedling when acne is present. By way of example, and not limitation, a person asked if microneedling over active acne causes infection. See: https://www.realself.com/question/penang-microneedling-active-acne-infection. Samer Muala, M.D. replied that "Yes it can. If you don't avoid the areas around the acne you can introduce the bacteria to other places." Id. Dr. Georges Kaado also replied to the same question, stating, "Yes active acne is a contraindication with microneedling. It can spread bacteria to other areas of the face and cause future breakouts." Id. Dr. Roberta Gartside, who also responded to that question, answered that, "Microneedling in the setting of active acne may lead to the spread of bacteria and infection. Microneedling may be done but the area of active acne must be avoided and by active, I mean, perhaps only a few small pustules and not red and inflamed." Id.

The website Banish.com who wrote "The Acne Battle Book" in 2021, wrote a blog article entitled, "Can You Microneedle On Active Acne? Why You Absolutely Shouldn't," located at https://banish.com/blogs/article/avoid-active-acne-a-pre-requisite-to-derma-rolling that states, "You absolutely should not dermaroll over any acne on the skin. This is because you would only further irritate the existing acne, and bacteria will be pressed on the needles and all those needles will just spread the bacteria further into other areas of the skin. Same thing goes for any other sort of skin rash or infection." The article further states, as a heading, "Microneedling over active acne can cause more acne."

Additional prior art that contraindicates the current invention was set forth in a video posted on YouTube at https://www.youtube.com/watch?v=LedxmgZ48eY by popular YouTube content creator, Sarah Perkins. In the video, entitled, "How to Microneedle with Active Acne", Ms. Perkins states, "you don't want to microneedle over active acne; not only would it really really hurt, but you definitely can transfer bacteria, you can actually make the wound even worse . . . " Id at 1:13-1:18. The website Healthline located at https://www.healthline.com, posted an article at https://www.healthline.com/health/microneedling-for-acne-scars entitled, "Can I Treat Acne Scars with Microneedling?" in which the site recommends microneedling for acne scarring but not for active acne. Specifically at the subheading entitled, "Side effects of microneedling for acne scars, Healthline states, "Your dermatologist may not recommend microneedling for your acne scars if you're currently experiencing an acne breakout. It's also not recommended if you have rosacea or eczema, as the procedure can worsen your symptoms." Another article on the site Healthline entitled, "Microneedling: The Latest Craze in Skin Care," at https://www.healthline.com/health-news/microneedling-latest-craze-in-skin-care shares a statement made by Tsippora Shainhouse, M.D., a dermatologist in Beverly Hills and clinical instructor at the University of Southern California, "If you have active acne, or tender acne cysts, do not microneedle over these areas. It will irritate the skin, make them more inflamed and potentially spread bacteria. Wait until your skin is more clear before attempting the procedure."

Cosmedia, a skincare company that specializes in acne and sells microneedling rollers, expressly states at https://cosmedica-skincare.com/blogs/news/what-you-need-to-know-about-microneedling-for-acne, in the section entitled "Is Microneedling Safe on Active Acne": "You should avoid doing a microneedling treatment on active acne that has open sores or intense irritation. All you have to do is wait for the acne to subside and treat it with the right skincare for acne, before starting any microneedling sessions. It's mainly going to be very beneficial in reducing the appearance of acne scars and marks on the skin that are making your complexion look less than optimal." A Pubmed search done immediately prior to filing this application for 'microneedling acne vulgaris' yielded 0 results. Further, a search for microneedling resulted only articles dealing with the treatment of acne scars.

James Fulton, MD, PhD, wrote on his company's website, VIVANT, at https://www.vivantskincare.com/blogs/doctors-tips/why-microneedling-and-acne-dont-mix that microneedling and acne do not mix. Specifically, Dr. Fulton states in the section entitled, "No Micro-needling on Active Acne!", Whether the dermaroller is a home care device or the type used by professionals, it is guaranteed to make acne worse if used over active lesions. If [ ] you have pustules, pimples, inflammation, nodules, or any form of active breakout, that is a flat NO to the roll. The needles will come into contact with acne bacteria under the surface of the skin and spread it, igniting more and worse flare-ups. Additionally, already inflamed skin will suffer from further irritation. The same caution applies to the skin with active eczema, psoriasis, or any other active irritation."

Northstar Dermatology writes of the benefits of microneedling on their website at https://www.northstardermatology.com/blog/benefits-of-microneedling-aging-acne-and-scars#:~:text=The%20simplest%2C%20most%20effective%20treatment&text=However%2C%20if%20someone%20has%20active,inflamed%2C%20and%20possibly%20spread%20bacteria but warns about microneedling over acne by stating, "However, if someone has active acne or cystic acne, the dermatologist will avoid microneedling over those areas. Microneedling over active acne can irritate acne further, make skin inflamed, and possibly spread bacteria."

PMU Hub states in an article entitled "Microneedling for Acne Scars—All You Need to Know" posted on a website located at https://www.pmuhub.com/microneedling/microneedling-for-acne-scars/that, "If you have active acne and you get microneedling over it, the bacteria can spread to the rest of the skin and cause a major breakout." It further states, "Microneedling shouldn't be used on active acne. Essentially, acne is pores clogged with sebum where bacteria develop. If they are opened with needles which go over skin that isn't infected, the bacteria spreads. Plus, the inflamed skin will get irritated further."

These and many other prior art articles and websites explain why the current invention which uses microneedling and a pure medical grade CBD oil is novel and non-obvious. The present invention challenges the prior art belief that microneedling alone or microneedling with pure medical grade oil is counterintuitive to a person skilled in the art.

Acne is a common skin condition that affects a large number of people, particularly teenagers and young adults. Acne can have a significant impact on a person's self-esteem, and many individuals have tried numerous treatments with little success. Furthermore, a study, conducted by the American Academy of Dermatology published in 2013 and revised in 2017 found that 50 million Americans suffer from acne each year, making it the most common skin condition in the United States. Additionally, a survey conducted by the National Rosacea Society found that 90% of acne sufferers experience a negative impact on their self-esteem, while 70% report feeling depressed or anxious as a result of their acne. Given these statistics and the emotional toll that acne can take on individuals, there is clearly a significant need for an easy and effective solution to treat acne. To date, the present invention has been shown to have promising results in treating acne, providing a potential solution to this long-felt but unsolved need. See: https://www.rosacea.org/patients/all-about-rosacea#:~:text=In%20surveys%20by%20the%20National, contact%20or%20cancel%20social%20engagements. The study and survey to which they cite is located at: https://pubmed.ncbi.nlm.nih.gov/29089180/ There is an additional study with similar survey results: https://www.ncbi.nlm.nih.gov/pmc/articles/PMC4031723/

SUMMARY OF THE INVENTION

The present invention describes a method for treating inflammatory skin conditions using a microneedle roller or a device using a plurality of fine needles for perforating the outer skin layer of a person with active acne or any inflammatory skin condition, such as, but not limited to, rosacea, eczema, psoriasis plaques, etc., in the presence of a medical grade oil that is specifically formulated to reduce inflammation or which naturally reduces inflammation and/or has antimicrobial and/or antioxidant properties. The microneedling allows the transdermal absorption of the oil into the acne pustules which reduces inflammation. In a preferred method of the present invention, the oil that is used is medical grade CBD oil because of its ability to penetrate the skin more effectively than other oils. CBD has anti-inflammatory properties which can reduce redness, swelling, and inflammation associated with acne. It also has antimicrobial properties, which help to kill the bacteria that contribute to acne so that the bacteria is not carried from pustule to pustule. Additionally, CBD has been shown to regulate the production of sebum, the oil that can contribute to acne when produced in excess. It also has antioxidant properties. By targeting multiple aspects of acne, CBD can provide a more comprehensive approach to acne treatment than just using microneedling or other anti-inflammatory' treatments, alone.

In a preferred method of the present invention for treating inflammatory skin conditions using a microneedling device, the method comprises cleaning the area to be treated, applying medical grade CBD oil to the area being treated, microneedling the area to be treated at a depth of approximately 1.0 mm, then microneedling the area being treated at a depth of approximately 1.5 mm, applying medical grade pure CBD tincture to the transdermal pathways created by the microneedling within 15 minutes of the last microneedling, leaving the applied CBD tincture on the treated areas for at least 15 minutes, repeating the treatment as prescribed by the doctor until the patient is satisfied with the level of the inflammatory skin condition and/or the inflammatory skin condition is gone.

In a preferred method of the present invention, the patient's face and/or treatment site(s) are washed with a gentle cleanser to ensure the area is clean.

In a preferred method of the present invention, numbing is applied to the patient's face and/or treatment site(s) which is removed after the treatment site(s) are numb.

In a preferred method of the present invention, approximately 0.5-1.0 mL of topical CBD tincture is applied both before and after microneedling the treatment site(s).

In a preferred method of the present invention, the oil applied after the microneedling is left on the patient. In another preferred method of the present invention, the oil applied after the microneedling is washed off with a gentle cleanser.

In a preferred method of the present invention, the method should be repeated every 3 weeks until the inflammatory skin condition is at a satisfactory level or is gone.

In a preferred method of the present invention, a commercial microneedling pen that is able to provide variability of depths which are controlled by the user is used. In another preferred method of the present invention, the micronee-
dling pen contains disposable needles or needle cartridge.

In a preferred method of the present invention, the tincture
comprises organic hempseed oil combined with medical
grade CBD isolate. In a preferred method of the present
invention, the tincture comprises 30 mL of organic hemp-
seed oil combined with 3000 mg of medical grade CBD
isolate. In yet another preferred method of the present
invention, the CBD isolate does not contain any other
cannabinoids, microbes and/or volatile chemicals. In an
alternate preferred embodiment of the present invention, any
medical grade anti-inflammatory antibacterial antioxidant
pure oil may be used.

BRIEF DESCRIPTION OF THE DRAWING

FIG. 1 is an illustration of the microneedling step of a
preferred method of the present invention, after the CBD or
other medical grade anti-inflammatory, antibacterial and
antioxidant pure oil has been applied to the patient's face in
the area to be microneedled.

DETAILED DESCRIPTION OF THE INVENTION

While various methods of the present invention are dis-
cussed in detail below, it should be appreciated that the
method of the present invention provides many applicable
inventive concepts that can be embodied in a wide variety of
specific contexts. The specific methods discussed herein are
merely illustrative of specific methods of the present inven-
tion and are not meant to limit the scope of the invention.

Terms used herein have meanings commonly understood
by a person of ordinary skill in the art relevant to the present
invention. Terms such as "a", "an" and "the" are not
intended to refer to only a singular entity but include the
general class of which a specific example may be used for
illustration. The terminology used herein describes specific
methods of the present invention but is not intended to limit
the invention.

The present invention is a method for treating inflamma-
tory skin conditions such as, but not limited to, acne,
rosacea, plaque psoriasis, and the like, using a sterile
microneedle roller or other puncturing device that contains
a plurality of fine needles whose depth can be controlled by
the user, after applying the treatment area with a medical
grade anti-inflammatory, antimicrobial, oil, such as, but not
limited to, a pure CBD isolate in an organic hempseed oil.

Microneedling can create thousands of microscopic chan-
nels during a single treatment in the epidermis of the of skin
of the treatment area on a patient so that the specific
anti-inflammatory antimicrobial ingredients are delivered
deep into the epidermis of the treatment area, while also
triggering a natural immune response to disinfect and
remove debris such as pus and bacteria, while increasing the
formation of new tissue by activating the production of
collagen and elastin as well as creating new capillaries to
improve the blood supply in the treated area.

In a preferred method of the present invention, the
microneedler is a commercial medical device for enhancing
transdermal delivery of specific ingredients which reduce
inflammation and promote healing. By way of example and
not limitation, such devices include, but are not limited to,
the CosmoPen by Cosmofrance and the Skinpen by Crown
Aesthetics which are microneedling devices with sterile
disposable heads containing multiple needles which allow
the user to control the depth of penetration of the needles into the skin of the patient. However, any microneedling or
stamping device with sterile needles of fixed depth may be
used as long as the needles can achieve a depth of 1.0 to 1.5
mm, and where the depth of the needle is controlled by the
user.

In a preferred method, the needles are disposable due to
possible contamination. They may be part of a disposable
cartridge that can be replaced after use. Non-disposable
needles could be used but they must be sterilized before and
after use. Since needles become dull after several uses,
non-disposable needles are not optimal. Thus, it is best to
use a microneedler or a puncturing device that uses dispos-
able needles, as they will be sharp during each use. In the
method of the present invention, the microneedler can be
used anywhere on the body except for the eyes, mouth,
nostrils, ears, and genital regions. The method of the present
invention should not be used on patients with active skin
cancer, open wounds, sores, or an allergy to the material
used to create the needles.

In a preferred method of the present invention, the patient
begins with a clean face devoid of makeup, creams, lotions,
or oils. In a preferred method of the present invention, prior
to microneedling, the patient or an assistant washes the
patient's face and/or treatment sites with a gentle cleanser.
A clean face minimizes the risk of infection and allows the
microneedling device to easily glide over the treatment area
to create tiny punctures that improve the absorption of the
medical grade anti-inflammatory oil applied during and after
treatment. A gentle cleanser is preferred as harsh soaps,
exfoliating scrubs, or disinfectants may cause drying, irri-
tation, skin sensitivity and even damage the epidermis.

In a preferred method of the present invention, numbing
cream may be applied prior to treatment and rinsed off
thoroughly before treatment. In an alternative preferred
method of the present invention, numbing is not required.

As shown in FIG. 1, in a preferred method of the present
invention, approximately 0.5-1.0 mL of medical grade topi-
cal CBD tincture 12 is applied to the treatment area 10 prior
to microneedling, however, any medical grade anti-inflam-
matory antimicrobial pure oil may be used. In addition to its
anti-inflammatory use during treatment, the oil assists the
microneedling device to easily glide over the skin in the
treatment area. The oil also creates a protective barrier so
that the treatment area is less vulnerable to bacteria, viruses
and other harmful substances that can cause inflammation,
breakouts, or other skin issues. The oil also hydrates,
soothes, and protects the treatment area during and after the
treatment. In a preferred method of the present invention, an
oil that contains essential fatty acids such as hempseed,
jojoba, rosehip, vitamin C or argan oil, helps to strengthen
the skin's barrier to improve its ability to retain moisture. In
an alternate preferred embodiment of the present invention,
any medical grade anti-inflammatory antibacterial antioxi-
dant pure oil with similar qualities to that of CBD may be
used.

In a preferred method of the present invention, as shown
in FIG. 1, after the oil 12 is applied to the treatment area 10,
the treatment area is microneedled by a physician, an
aesthetic technician or the like using a microneedler 14 with
a removable and replaceable needle cartridge 16. When the
method of the present invention is used to treat active acne,
the microneedling allows the transdermal absorption of the
oil into the acne pustules to reduce inflammation.

In a preferred method of the present invention, the area to
be treated is first microneedled at a depth of approximately
1.0 mm and then microneedled at a depth of approximately
1.5 mm. Thereafter, medical grade pure CBD tincture is applied to the transdermal pathways created by the microneedling within 15 minutes of the last microneedling. In a preferred method of the present invention, approximately 0.5-1.0 mL of medical grade topical CBD tincture is applied to the treatment area both before and after microneedling. In a preferred method of the present invention, the applied CBD tincture is left on the treated areas for at least 15 minutes. In yet another preferred method of the present invention, the method of the present invention is repeated as prescribed by the doctor after several days have lapsed until the patient is satisfied with the level of the inflammatory skin condition and/or the inflammatory skin condition is gone.

In a preferred method of the present invention, a CBD isolate is suspended in hempseed oil. In a preferred method of the present invention, the amount and concentration of CBD needed for an effective microneedling treatment can vary depending on factors such as the severity of the condition being treated, the area of the body being treated, and the specific formulation being used. A tincture with a 3000 mg concentration of CBD has been shown to be most effective. A tincture with less total CBD strength could also be effective depending on the treatment area and the condition being treated. For some conditions, a 25 mg pure CBD tincture may be used while for other conditions, a 10,000 mg tincture may be used. The oil is made by removing any contaminants, THC, other cannabinoids, microbes, or volatile chemicals, so that the oil is as pure as possible. In a preferred method of the present invention, any medical grade antibacterial oil which has anti-sebum producing qualities and in which there is less than 100 CFU/g of Total aerobic bacterial count, total coliform bacterial count, total bile tolerant gram-negative count, and total yeast & mold count is used. In a preferred method of the present invention, the oil is tested to ensure there are no detectable levels of propane, isobutane, butane, methanol, pentane, ethanol, acetone, isopropanol, acetonitrile, hexane, or heptane.

The purity of the oil being used is extremely important for microneedling for inflammatory conditions and especially when active acne pustules are present because during the treatment, the skin is punctured with tiny needles, creating hundreds to thousands of microchannels that can allow substances to penetrate more deeply into the skin. If impure or contaminated products are used during a microneedling treatment, there is a risk of introducing harmful substances which can lead to infection, allergic reactions, or other adverse effects. In a preferred method of the present invention, HealMD's CBD tincture is used, however other medical grade pure anti-inflammatory, antimicrobial and antioxidant CBD oils may be used.

The medical grade pure CBD tincture as fabricated above reduces inflammation by targeting receptors of the skin that elicit a response from the body's endocannabinoid system (ECS). The ECS is a complex system of receptors and neurotransmitters that plays a role in regulating physiological processes, including pain, inflammation, immune function, and mood. The ECS is found throughout the body, including in the skin, where it helps to maintain skin homeostasis and promote healthy skin function. CBD and other cannabinoids found in hemp seed oil interact with the ECS by binding to the body's CB1 and CB2 receptors, which are found throughout the body, including in the skin. When CBD binds to these receptors, it helps modulate the immune response and reduce inflammation, which soothes and calms irritated skin by reducing the production of inflammatory cytokines such as tumor necrosis factor alpha (TNF-a). Hempseed oil is also rich in essential fatty acids, which also aids in reducing inflammation and supports healthy skin function. Essential fatty acids, such as omega-3 and omega-6 are important building blocks of healthy skin cells and strengthens the skin's barrier function and improves its ability to retain moisture. By targeting receptors in the skin and eliciting a response from the ECS, CBD combined with hempseed oil reduces inflammation and promotes healthy, radiant skin.

CBD and hempseed oil also have antioxidant properties, which aids in reducing the production of reactive oxygen species (ROS). ROS are molecules that are produced as a byproduct of normal cellular metabolism that can cause oxidative damage to cells and tissues. This damage leads to inflammation and other cellular dysfunction. By reducing ROS production, CBD isolate suspended in hempseed oil reduce inflammation and promote healthy cellular function. In addition to their effects on the immune system and oxidative stress, CBD and hempseed oil interacts with other receptors and signaling pathways that are involved in inflammation. For example, CBD can activate the PPAr-gamma receptor, which is involved in regulating inflammation and immune function. By activating this receptor, CBD reduces inflammation and promote healthy immune function.

CBD is involved in cell-growth differentiation and aids the body in regulating the production of sebum, the oily substance that is produced by the sebaceous glands in the skin. While sebum is important for keeping the skin hydrated and healthy, excess production of sebum contributes to skin problems such as acne. CBD works as a sebostatic agent by interacting with the endocannabinoid system, which plays a key role in regulating various physiological processes in the body, including the production of sebum. When CBD is applied to the skin, it activates the CB2 receptors that are found on the sebaceous glands to modulate the production of sebum and reduce its overproduction. In addition to its direct effects on sebum production, CBD also has anti-inflammatory properties that reduces the inflammation associated with acne. Inflammation is a key factor in the development of acne, and by reducing this inflammation, CBD aids in preventing the formation of acne lesions. Thus, CBD has the unique capability to eliminate active acne more than other pharmaceutical medications, with lower risks and side effects.

CBD also has been shown to have antibacterial properties against a variety of bacteria by disrupting the bacterial membrane: CBD interacts with the bacterial membrane causing it to become more permeable and less stable. This disruption leads to the leakage of essential nutrients and ions and can eventually causes the bacteria to die. It also interferes with the metabolic processes of bacteria, inhibiting their ability to generate energy and produce essential molecules like proteins and DNA. CBD also modulates the body's immune response; CBD can interact with the immune system to help regulate the body's response to bacterial infections. By modulating the immune response, CBD can help to reduce inflammation and prevent the overproduction of pro-inflammatory cytokines that can contribute to bacterial growth and spread.

CBD also works synergistically with other antibacterial agents to enhance their effectiveness. For example, in combination with antibiotics, CBD has been shown to improve the effectiveness of the antibiotics against certain types of bacteria.

The present disclosed methods are to be considered in all respects as illustrative and not restrictive, the scope of the invention being indicated by the appended claims rather than in the foregoing description, and all changes which come within the meaning and range of equivalency of the claims are therefore intended to be embraced therein. The methods described herein are exemplary and preferred methods of the present invention. And while these preferred methods and techniques of the present invention have been shown herein, it should be understood that many changes, substitutions and/or modifications may be made by those persons skilled in the art. It should be appreciated from the description set forth herein of the presently preferred method that other methods are possible and within the scope of the present invention. Thus, the present invention is not intended to be limited to the particular methods specifically discussed herein.

While all of the methods of the present invention disclosed and claimed herein have been described in terms of preferred methods, it will be apparent to those skilled in the art that numerous variations may be applied to the methods and in the steps or in the sequence of steps of the method described herein without departing from the spirit and scope of the invention. All such similar substitutes and modifications apparent to those skilled in the art come within the spirit and scope of the invention as defined by the appended claims.

What is claimed is:

1. A method for treating an inflammatory skin condition in a patient in an area other than the genitals, eyes, nose or mouth using a microneedling device having sterile needles capable of causing microscopic holes in the skin at a depth controlled by the user, comprising:
   cleaning the patient's treatment area,
   applying a first medical grade anti-inflammatory antibacterial antioxidant pure oil to the patient's treatment area,
   microneedling the patient's treatment area at a depth of approximately 1.0 mm to create transdermal pathways,
   microneedling the patient's treatment area at a depth of approximately 1.5 mm to create transdermal pathways,
   applying a second medical grade anti-inflammatory antibacterial antioxidant pure oil to the transdermal pathways within 15 minutes of one or both microneedling steps,
   leaving the applied second medical grade anti-inflammatory antibacterial antioxidant pure oil on the patient's treatment area for at least 15 minutes,
   repeating the treatment until the patient is satisfied with the level of the inflammatory skin condition or the inflammatory skin condition is gone.

2. The method of claim 1, wherein the step of cleaning the patient's treatment area comprises washing the patient's treatment area with a gentle cleanser to ensure the area is clean.

3. The method of claim 1, further comprising the step of applying a numbing product to the patient's treatment area after the cleansing step and removing the numbing product after the patient's treatment area is numb prior to microneedling.

4. The method of claim 1, wherein the amount of the first or second medical grade anti-inflammatory antibacterial antioxidant pure oil applied to the patient's treatment area is approximately 0.5-1.0 mL.

5. The method of claim 1, wherein the second medical grade anti-inflammatory antibacterial antioxidant pure oil applied after the microneedling step is left on the patient's treatment area and not removed.

6. The method of claim 1, wherein the second medical grade anti-inflammatory antibacterial antioxidant pure oil applied after the microneedling is washed off with a gentle cleanser after at least 15 minutes.

7. The method of claim 1, wherein all the steps are repeated after at least several days have lapsed until the inflammatory skin condition is at a satisfactory level or is gone.

8. The method of claim 1, wherein the first or second medical grade anti-inflammatory antibacterial antioxidant pure oil is a CBD tincture comprising 30 mL of organic hempseed oil and 3000 mg of medical grade CBD isolate.

9. The method of claim 1, wherein the first and second medical grade anti-inflammatory antibacterial antioxidant pure oils are the same.

10. The method of claim 1, wherein the medical grade anti-inflammatory antibacterial antioxidant pure oil comprises 25 mg to 10,000 mg of CBD.

11. A method for treating acne in a patient using a microneedling device having sterile needles capable of causing microscopic holes in the skin at a depth controlled by the user, comprising:
   cleaning the patient's treatment area,
   applying a first medical grade pure CBD tincture to the patient's treatment area,
   microneedling the patient's treatment area at a depth of approximately 1.0 mm to create transdermal pathways,
   microneedling the patient's treatment area at a depth of approximately 1.5 mm to create transdermal pathways,
   applying a second medical grade pure CBD tincture to the transdermal pathways within 15 minutes of one or both the last microneedling steps,
   leaving the second medical grade pure applied CBD tincture on the patient's treatment areas for at least 15 minutes,
      repeating the treatment until the patient is satisfied with the level of the acne remaining or until the acne in the treatment area is gone.

12. The method of claim 11, wherein the step of cleaning the patient's treatment area comprises washing the patient's treatment area with a gentle cleanser to ensure the patient's treatment area is clean.

13. The method of claim 11, further comprising the step of applying a numbing product to the patient's treatment area after the cleaning step and removing the numbing product after the patient's treatment area is numb prior to microneedling.

14. The method of claim 11, where the steps of applying the first or second medical grade pure CBD tincture comprises applying approximately 0.5-1.0 mL of a medical grade pure CBD tincture.

15. The method of claim 11, wherein the second medical grade pure CBD tincture applied after microneedling is left on the patient's treatment area and not removed.

16. The method of claim 11, wherein the second medical grade pure CBD tincture applied after the microneedling is washed off with a gentle cleanser.

17. The method of claim 11, wherein the steps are repeated every 3 weeks until acne is at a satisfactory level or is gone.

18. The method of claim 11, wherein the medical grade pure CBD tincture comprises 30 mL of organic hempseed oil and 3000 mg of medical grade pure CBD isolate.

19. The method of claim 11, wherein the first and second medical grade pure CBD tinctures are the same.

20. The method of claim 11, wherein the medical grade pure CBD tincture comprises 25 mg to 10,000 mg of CBD.

* * * * *